United States Patent
Kobayashi et al.

(10) Patent No.: US 12,092,570 B2
(45) Date of Patent: Sep. 17, 2024

(54) SPECIFIC COMPONENT DETECTION METHOD, DETERMINATION METHOD, AND APPARATUSES USING THESE METHODS

(71) Applicant: THE UNIVERSITY OF TOKYO, Tokyo (JP)

(72) Inventors: Yohei Kobayashi, Tokyo (JP); Shuntaro Tani, Tokyo (JP); Hiroharu Tamaru, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 210 days.

(21) Appl. No.: 17/802,695

(22) PCT Filed: Feb. 26, 2021

(86) PCT No.: PCT/JP2021/007462
§ 371 (c)(1),
(2) Date: Aug. 26, 2022

(87) PCT Pub. No.: WO2021/172541
PCT Pub. Date: Sep. 2, 2021

(65) Prior Publication Data
US 2023/0145009 A1 May 11, 2023

(30) Foreign Application Priority Data
Feb. 27, 2020 (JP) .................. 2020-031615

(51) Int. Cl.
*G01N 21/3504* (2014.01)
*G01N 33/00* (2006.01)

(52) U.S. Cl.
CPC ..... *G01N 21/3504* (2013.01); *G01N 33/0027* (2013.01); *G01N 2201/0634* (2013.01)

(58) Field of Classification Search
CPC .............. G01N 21/3504; G01N 33/00; G01N 33/0027; G01N 2201/0634;
(Continued)

(56) References Cited

U.S. PATENT DOCUMENTS 11,262,315 B2 * 3/2022 Kanemoto ......... G01N 21/8806
2015/0346609 A1 12/2015 Den Boef
(Continued)

FOREIGN PATENT DOCUMENTS

JP 2005-257358 A 9/2005
JP 2011-102747 A 5/2011
(Continued)

OTHER PUBLICATIONS

Apr. 27, 2021 International Search Report issued in International Patent Application No. PCT/JP2021/007462.
(Continued)

*Primary Examiner* — Jurie Yun
(74) *Attorney, Agent, or Firm* — Oliff PLC (57) ABSTRACT

A configuration of the present disclosure specifies a signal point of a specific component and a background point, based on time series two-dimensional spectroscopic image data of a gas; calculates a correlation coefficient between a time series detection signal at the signal point and a time series detection signal at the background point; and generates a time series detection signal of the specific component, based on a corrected time series detection signal obtained by subtracting a product of the correlation coefficient and the time series detection signal at the background point from the time series detection signal at the signal point.

12 Claims, 6 Drawing Sheets

(58) Field of Classification Search
CPC .. G01N 2201/1296; G01J 3/1809; G01J 3/28; G01J 3/2823; G01J 3/42; G01J 3/457
See application file for complete search history.

(56) References Cited

U.S. PATENT DOCUMENTS

2018/0087961 A1   3/2018   Noda
2019/0104941 A1   4/2019   Yamamoto et al.

FOREIGN PATENT DOCUMENTS

| JP | 2015-510126 A | 4/2015 |
| JP | 2018-54337 A | 4/2018 |
| JP | 2019-88773 A | 6/2019 |
| JP | 2019-109374 A | 7/2019 |

OTHER PUBLICATIONS

Zhu, Xiao Xiang et al., "Deep Learning in Remote Sensing", IEEE Geoscience and Remote Sensing Magazine, vol. 5, Issue 4, pp. 8-36, Dec. 27, 2017.
Nugent-Glandorf et al., "Mid-infrared virtually imaged phased array spectrometer for rapid and broadband trace gas detection", Optics Letters, Aug. 1, 2012, vol. 37, No. 5, pp. 3285-3287.
Feb. 8, 2024 Partial Supplementary Search Report issued in European Patent Application No. 21761446.0.

\* cited by examiner

SPECIFIC COMPONENT DETECTION METHOD, DETERMINATION METHOD, AND APPARATUSES USING THESE METHODS

TECHNICAL FIELD

The present disclosure relates to a specific component detection method, a determination method, and apparatuses using these methods and more specifically relates to a specific component detection method of properly detecting a time series detection signal of a specific component included in a gas, a specific component detection apparatus using this method, a determination method of determining a state based on a component included in a gas, and a determination apparatus using a learned model of this method.

BACKGROUND ART

A proposed configuration of an apparatus for detecting a specific component included in a gas uses a measurement output of light having a wavelength that is not easily absorbed in infrared light transmitted through an atmospheric gas, so as to normalize other measurement outputs (as described in, for example, Patent Literature 1). This apparatus disperses the infrared light transmitted through the atmospheric gas and performs normalization by dividing a light-receiving wavelength signal based on the intensity of light, which is obtained by a plurality of detectors, each being configured to detect the intensity of light having a wavelength absorbed by a predetermined component, out of dispersed light components, by a signal based on the intensity of light, which is obtained by a detector configured to detect the intensity of light having a wavelength that is not absorbed by the predetermined component, out of the dispersed light components.

A proposed configuration of an apparatus for determining a state based on a component included in a gas performs measurement by causing a sensor array provided with a plurality of sensors having different degrees of hydrophilicity, different degrees of hydrophobicity, different electric charges, different electric conductivities or the like, which are obtained by surface treatment of the sensors, to come into contact with expiration (as described in, for example, Patent Literature 2). This apparatus uses the sensor array provided with the plurality of sensors to obtain a profile of expiration of a human subject (or an animal subject) defined by the amounts and the types of components included in the expiration. This apparatus measures a profile of expiration components without performing separated identification of individual molecular species constituting a volatile organic compound included in the expiration.

CITATION LIST

Patent Literature

PTL 1: JP2005-257358
PTL 2: JP2011-102747

SUMMARY

Technical Problem

The apparatus for detecting the specific component included in the gas described above is, however, likely to have an insufficient SN ratio relative to the normalized signal. Especially in the case where the measurement output is time series data, a time change in the light having the wavelength that is not absorbed by the predetermined component out of the dispersed lights fails to perform proper normalization.

Furthermore, the apparatus for determining the state based on the component included in the gas, on the other hand, requires the sensor array provided with the plurality of sensors having different degrees of hydrophilicity, different degrees of hydrophobicity, different electric charges, different electric conductivities or the like. The analysis based on the hydrophilicity, the hydrophobicity, the electric charge or the electric conductivity, however, has a low accuracy in identification of the component included in the expiration and does not allow for proper determination.

A specific component detection method and an apparatus using this method mainly aims to detect a specific component included in a gas with higher sensitivity.

A determination method and an apparatus using this method mainly aims to determine a state more properly.

Solution to Problem

In order to achieve the main objects described above, the specific component detection method, the determination method, and the apparatuses using these methods of the present disclosure have configurations described below.

According to one aspect of the present disclosure, there is provided a specific component detection method of properly detecting a time series detection signal of a specific component included in a gas. The specific component detection method comprises an input step of receiving an input of time series two-dimensional spectroscopic image data of the gas; a specification step of specifying a signal point of the specific component and a background point, based on the time series two-dimensional image data; a correlation coefficient calculation step of calculating a correlation coefficient between a time series detection signal at the signal point and a time series detection signal at the background point; and a signal generation step of generating a time series detection signal of the specific component, based on a corrected time series detection signal obtained by subtracting a product of the correlation coefficient and the time series detection signal at the background point from the time series detection signal at the signal point.

The specific component detection method according to this aspect of the present disclosure receives an input of time series two-dimensional spectroscopic image data of a gas and specifies a signal point of a specific component and a background point, based on the input time series two-dimensional image data. The time series two-dimensional image data is image data obtained with elapse of time by two-dimensionally dispersing the transmitted light, which is radiated from a light source for radiation of mid-infrared light and is transmitted through the gas. The mid-infrared light corresponds to light having a wavelength of 2 μm to 20 μm. The signal point is a point having a wavelength absorbed by the specific component, among respective points constituting a two-dimensional spectroscopic image. The background point is a point having a wavelength of little absorption over a time period when the time series two-dimensional spectroscopic image data are obtained, among the respective points constituting the two-dimensional spectroscopic image. Any of various techniques may be employed to specify the background point: for example, a technique of calculating correlation coefficients including self correlation with regard to respective points of a two-dimensional spectroscopic image and specifying a point having a small correction coefficient as a background point; or a technique of specifying a background point, based on a total sum or an average of detection values in time series of detection intensities at respective points of a two-dimensional spectroscopic image. The specific component detection method of this aspect subsequently calculates a correlation coefficient between a time series detection signal at the signal point and a time series detection signal at the background point, and generates a time series detection signal of the specific component, based on a corrected time series detection signal obtained by subtracting a product of the correlation coefficient and the time series detection signal at the background point from the time series detection signal at the signal point. The configuration of this aspect specifies the background point, based on the time series two-dimensional image data. This configuration accordingly specifies the background more appropriately and enables the time series detection signal of the specific component included in the gas to be obtained more properly. As a result, this enables the specific component included in the gas to be detected with higher sensitivity. The two-dimensional spectroscopic image data includes an image itself. The same shall apply hereinafter in the description. The corrected time series detection signal may be used as the time series detection signal of the specific component, or the time series detection signal of the specific component may be generated by processing the corrected time series detection signal by an enhancement process or a correction process.

In the specific component detection method of the above aspect, the signal generation step may comprise a step of processing the corrected time series detection signal by a low-pass filter, so as to generate the time series detection signal of the specific component. This configuration removes high-frequency noise and enables the specific component included in the gas to be detected with higher sensitivity.

In the specific component detection method of the above aspect, the time series two-dimensional spectroscopic image data may comprise data obtained by a high order diffraction grating configured to disperse light to high order diffraction light and a spectrometer placed at a location where high order diffraction lights obtained by the high order diffraction grating overlap with each other. In this aspect, the high order diffraction grating used may be an Echelle diffraction grating.

According to another aspect of the present disclosure, there is provided a specific component detection apparatus configured to detect a specific component by using the specific component detection method described in any of the above aspects of the present disclosure. More specifically, there is provided a specific component detection apparatus configured to detect a specific component by basically using a specific component detection method of properly detecting a time series detection signal of a specific component included in a gas and more specifically by using the specific component detection method comprising: an input step of receiving an input of time series two-dimensional spectroscopic image data of the gas; a specification step of specifying a signal point of the specific component and a background point, based on the time series two-dimensional image data; a correlation coefficient calculation step of calculating a correlation coefficient between a time series detection signal at the signal point and a time series detection signal at the background point; and a signal generation step of generating a time series detection signal of the specific component, based on a corrected time series detection signal obtained by subtracting a product of the correlation coefficient and the time series detection signal at the background point from the time series detection signal at the signal point.

The specific component detection apparatus of the above aspect detects the specific component by using the specific component detection method described in any of the above aspects of the present disclosure. Accordingly, the specific component detection apparatus of the present disclosure has advantageous effects similar to those of the specific component detection method of the present disclosure described above, i.e., the advantageous effect of specifying the background more appropriately, the advantageous effect of enabling the time series detection signal of the specific component included in the gas to be obtained more properly, and the resulting advantageous effect of enabling the specific component included in the gas to be detected with higher sensitivity.

The specific component detection apparatus of the above aspect may comprise a light source configured to irradiate a gas including a detection object with mid-infrared light; a two-dimensional spectroscopic diffractometer configured to two-dimensionally disperse and diffract mid-infrared light radiated from the light source and transmitted through the gas; and an arithmetic unit configured to generate a time series detection signal of the specific component, based on time series two-dimensional spectroscopic image data obtained by the two-dimensional spectroscopic diffractometer.

According to another aspect of the present disclosure, there is provided a determination method of determining a state based on a component included in a gas. The determination method comprises applying a learned model, which is obtained by machine learning using a plurality of two-dimensional spectroscopic image data of the gas as an input data set and a state based on the component in the gas as teacher data, to two-dimensional spectroscopic image data of the gas, so as to estimate a state.

The determination method according to this aspect of the present disclosure estimates a state by applying a learned model, which is obtained by machine learning using a plurality of two-dimensional spectroscopic image data of a gas as an input data set and a state based on a component of the gas as teacher data, to two-dimensional spectroscopic image data of the gas. This configuration enables the state to be determined more properly with regard to the two-dimensional spectroscopic image data of the gas. The determination method of the present disclosure may serve as a method of diagnosing a disease name based on expiration by using "expiration" as the "gas" and using the "name of disease" as the "state", may serve as a method of checking the state of an engine based on a combustion gas by using the "combustion gas of the engine" as the "gas" and using the "state of the engine" as the "state", and may serve as a method of checking the comfort of a closed space such as a private room based on the air in the space by using the "air in the closed space such as the private room" as the "gas" and using the "comfort of a person who is present in the closed space such as the private room" as the "state". In an example of application, the method may be employed in a vehicle and may be used for the purpose of health care check during driving. In another example of application, the method may be employed in a conference hall or a shop and may be used for the purpose of security, such as detection of explosives. The determination method of this aspect may be configured to perform machine learning by using the plurality of two-dimensional spectroscopic image data of the gas as an input data set and the state based on the component of the gas as teacher data or may be configured not to perform machine learning but to use a learned model obtained by machine learning.

In the determination method of the above aspect, the two-dimensional spectroscopic image data may comprise data obtained by a high order diffraction grating configured to disperse light to high order diffraction light and a spectrometer placed at a location where high order diffraction lights obtained by the high order diffraction grating overlap with each other. In this aspect, the high order diffraction grating used may be an Echelle diffraction grating.

In the determination method of the above aspect, the plurality of two-dimensional spectroscopic image data of the gas may comprise a plurality of time series two-dimensional spectroscopic image data of the gas. The configuration of this aspect uses a more appropriate learned model and thus enables the state to be estimated more properly.

According to another aspect of the present disclosure, there is provided a determination apparatus configured to determine a state by using the determination method described in any of the above aspects of the present disclosure. More specifically, there is provided a determination apparatus configured to determine a state by basically using a determination method of determining a state based on a component included in a gas and more specifically by using the determination method comprising applying a learned model, which is obtained by machine learning using a plurality of two-dimensional spectroscopic image data of the gas as an input data set and a state based on the component in the gas as teacher data, to two-dimensional spectroscopic image data of the gas, so as to estimate a state.

The determination apparatus of the above aspect determines the state by using the determination method described in any of the above aspects of the present disclosure. Accordingly, the determination apparatus of the present disclosure has advantageous effects similar to those of the determination method of the present disclosure described above, i.e., the advantageous effect of enabling the state to be determined more properly with regard to the two-dimensional spectroscopic image data of the gas. The determination apparatus of the present disclosure may serve as an apparatus for diagnosing a disease name based on expiration by using "expiration" as the "gas" and using the "name of disease" as the "state", may serve as an apparatus for checking the state of an engine based on a combustion gas by using the "combustion gas of the engine" as the "gas" and using the "state of the engine" as the "state", and may serve as an apparatus for checking the comfort of a closed space such as a private room based on the air in the space by using the "air in the closed space such as the private room" as the "gas" and using the "comfort of a person who is present in the closed space such as the private room" as the "state". The determination apparatus of this aspect may be configured to perform machine learning by using the plurality of two-dimensional spectroscopic image data of the gas as an input data set and the state based on the component of the gas as teacher data or may be configured not to perform machine learning but to use a learned model obtained by machine learning.

The determination apparatus of the above aspect may comprise a light source configured to irradiate a gas including a detection object with mid-infrared light; a two-dimensional spectroscopic diffractometer configured to two-dimensionally disperse and diffract mid-infrared light radiated from the light source and transmitted through the gas; and an arithmetic unit configured to estimate a state, based on two-dimensional spectroscopic image data obtained by the two-dimensional spectroscopic diffractometer.

DESCRIPTION OF EMBODIMENTS

Figure 1:
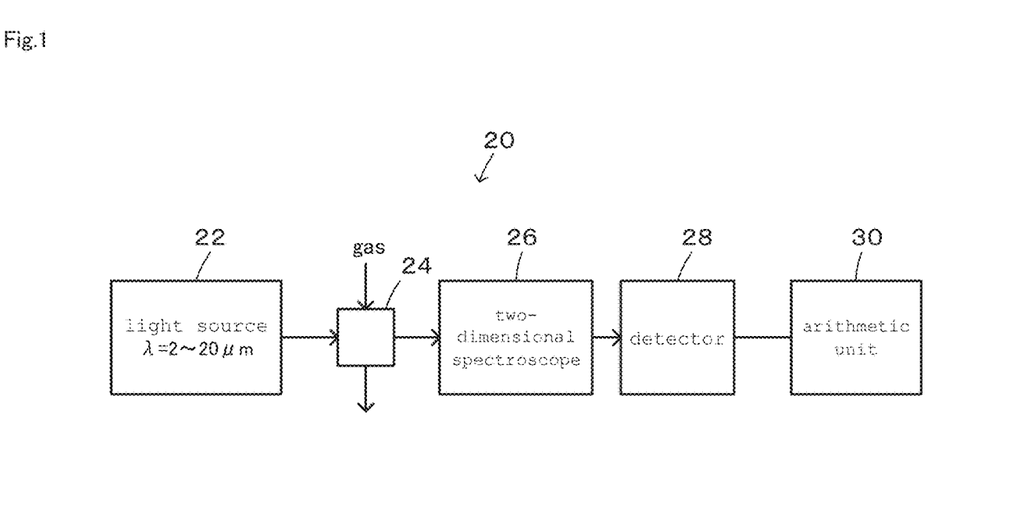
FIG. 1 is an explanatory diagram illustrating the schematic configuration of a specific component detection apparatus 20 according to a first embodiment.

The following describes embodiments of the present disclosure. FIG. 1 is an explanatory diagram illustrating the schematic configuration of a specific component detection apparatus 20 according to a first embodiment. As shown in FIG. 1, the specific component detection apparatus 20 according to the first embodiment includes a light source 22 configured to irradiate a gas introduced into a sample introducing portion 24 with light in a mid-infrared range (light having a wavelength of 2 μm to 20 μm); a two-dimensional spectroscope 26 configured to two-dimensionally disperse light transmitted through the gas in the sample introducing portion 24 and generate a two-dimensional spectroscopic image; a detector 28 configured to detect a light intensity of each pixel (area) of the two-dimensional spectroscopic image; and an arithmetic unit 30 configured to detect a specific component, based on data of light intensity of the two-dimensional spectroscopic image in time series (time series two-dimensional spectroscopic image data). Two-dimensional spectroscopic image data herein includes a two-dimensional spectroscopic image itself. The same shall apply hereinafter.

The two-dimensional spectroscope 26 is comprised of: a high order diffraction grating, such as an Echelle diffraction grating, configured to disperse light to high order diffraction light; and a spectrometer placed at a location where high order diffraction lights obtained by the high order diffraction grating overlap with each other, and is configured to two-dimensionally disperse light and generate a two-dimensional spectroscopic image (for example, an echellegram). The detector 28 is a known detector configured to convert a light intensity in each pixel (area) of the two-dimensional spectroscopic image into a voltage signal.

The arithmetic unit 30 is configured as a CPU-based general purpose computer and includes, for example, a ROM that stores processing programs and the like, a RAM that temporarily stores data, a flash memory, a storage device, and input/output ports, in addition to a CPU.

Figure 2:
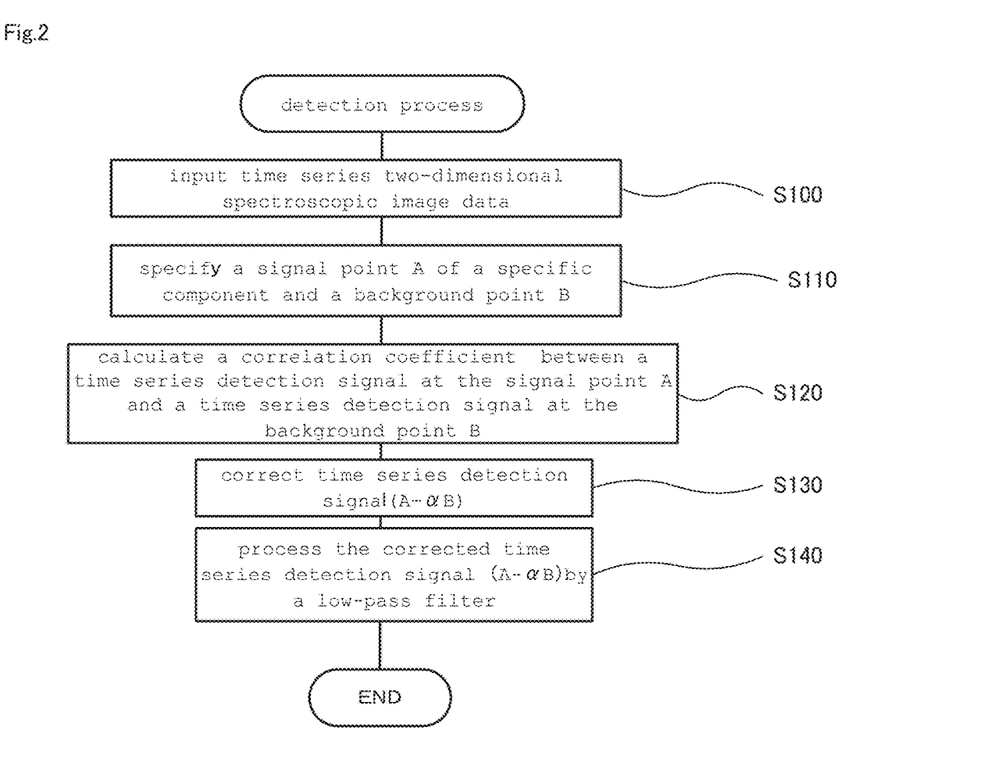
FIG. 2 is a flowchart showing one example of a detection process performed by an arithmetic unit 30.

The arithmetic unit 30 performs a detection process illustrated in FIG. 2. The detection process receives an input of time series two-dimensional spectroscopic image data detected by the detector 28 (step S100) and specifies a signal point A of a specific component and a background point B, based on the time series two-dimensional spectroscopic image data (step S110). The signal point A of the specific component is a point (pixel, area) having a wavelength absorbed by the specific component, among respective points (pixels, areas) constituting a two-dimensional spectroscopic image.

Accordingly, the signal point A is specified by determining the specific component. The background point B is a point (pixel, area) having a wavelength of little absorption over a time period when the time series two-dimensional spectroscopic image data are obtained, among the respective points (pixels, areas) constituting the two-dimensional spectroscopic image. Any of various techniques may be employed to specify the background point B: for example, a technique of calculating correlation coefficients including self correlation with regard to respective points of a two-dimensional spectroscopic image and specifying a point having a small correction coefficient as a background point; or a technique of specifying a background point, based on a total sum or an average of detection values in time series of detection intensities at respective points of a two-dimensional spectroscopic image.

The detection process subsequently calculates a correlation coefficient α between a time series detection signal at the signal point A and a time series detection signal at the background point B (step S120). The detection process then calculates a corrected time series detection signal (A-αB) by subtracting the product of the time series detection signal at the background point B and the correlation coefficient α from the time series detection signal at the signal point A (step S130). The detection process subsequently processes the corrected time series detection signal (A-αB) by a low-pass filter to generate a specific component time series detection signal (step S140) and is then terminated. The low-pass filter used is a filter that passes signals with frequencies of 10 Hz to 30 Hz.

Figure 3:
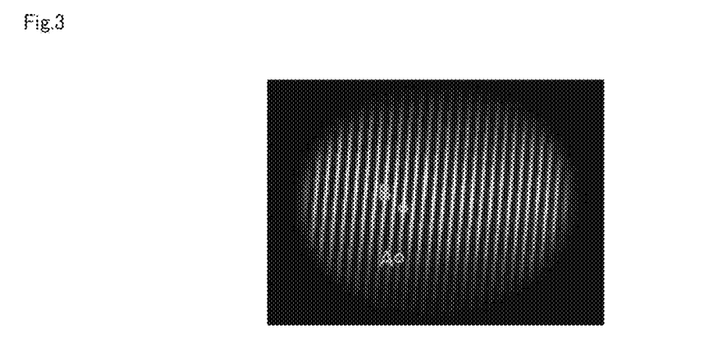
FIG. 3 is an explanatory diagram illustrating an echellegram as one example of a two-dimensional spectroscopic image in the case of introducing ethylene into a sample introducing portion 24.
Figure 4:
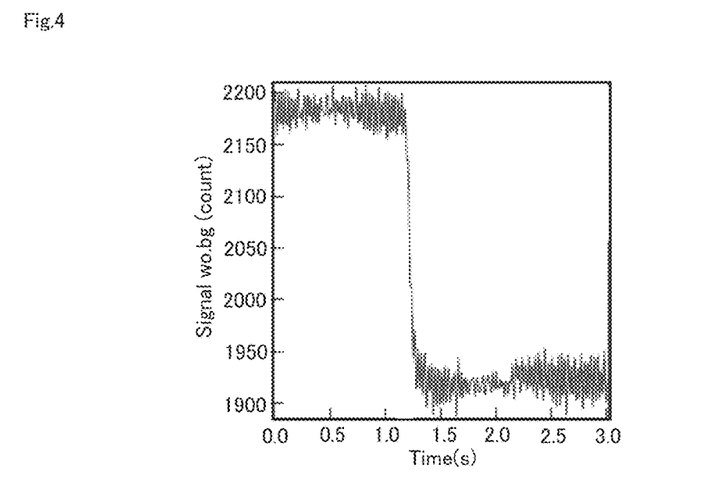
FIG. 4 is a graph of a time series detection signal at a signal point A in the case of introducing ethylene into the sample introducing portion 24.
Figure 5:
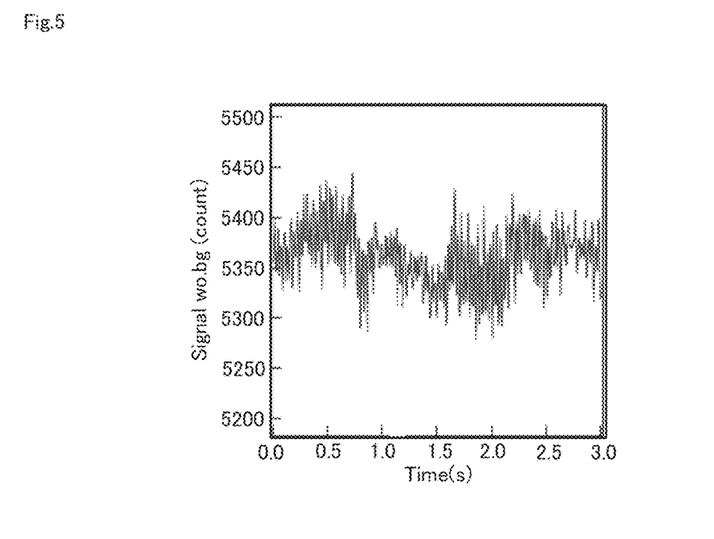
FIG. 5 is a graph of a time series detection signal at a background point B in the case of introducing ethylene into the sample introducing portion 24.
Figure 6:
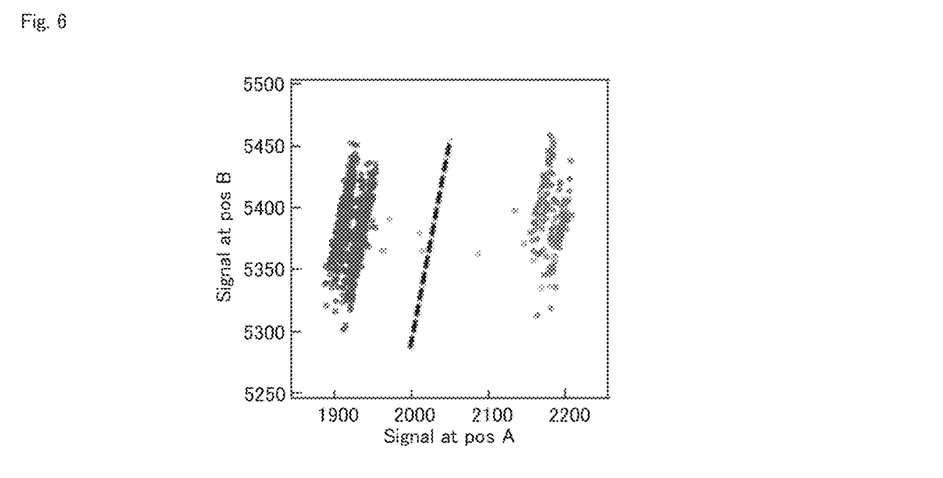
FIG. 6 is an explanatory diagram illustrating parametric plots of the signal point A and the background point B.
Figure 7:
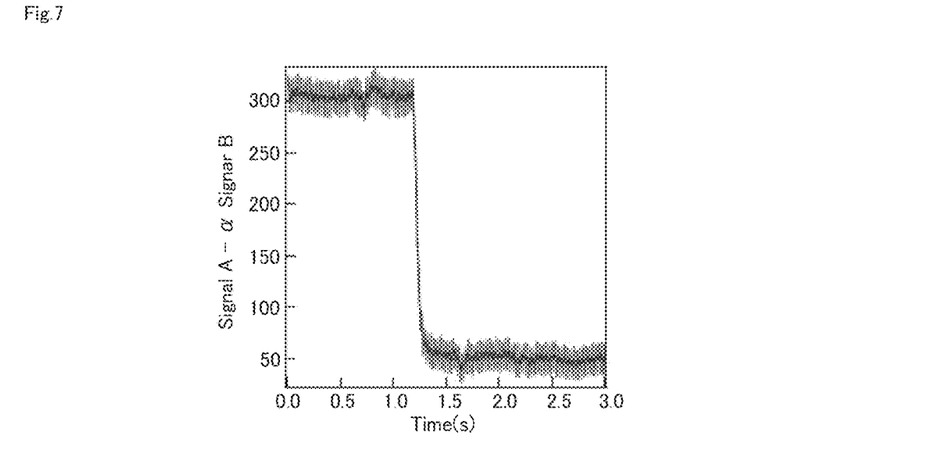
FIG. 7 is a graph of a specific component time series detection signal in the case of introducing ethylene into the sample introducing portion 24.
Figure 8:
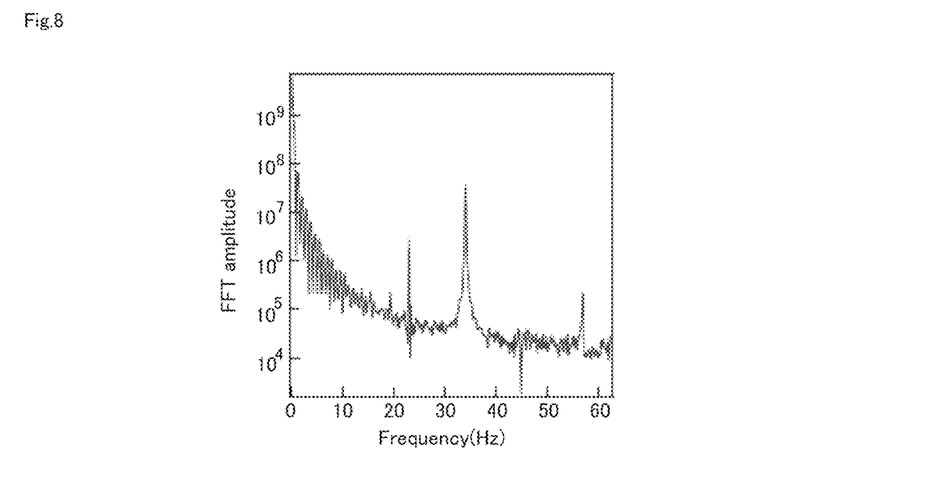
FIG. 8 is an explanatory diagram illustrating a Fourie spectrum of vibration of the specific component time series detection signal.

FIG. 3 is an explanatory diagram illustrating an echellegram as one example of a two-dimensional spectroscopic image in the case of introducing ethylene into a sample introducing portion 24. In FIG. 3, a circle A represents the signal point A, and a circle B represents the background point B. FIG. 4 is a graph of a time series detection signal at a signal point A in the case of introducing ethylene into the sample introducing portion 24. FIG. 5 is a graph of a time series detection signal at a background point B in the case of introducing ethylene into the sample introducing portion 24. FIG. 6 is an explanatory diagram illustrating parametric plots using a signal intensity at the signal point A and a signal intensity at the background point B as parameters. In FIG. 6, a right-side plot of detection signal is obtained in a vacuum state without introduction of a gas, and a left-side plot of detection signal is obtained in a gas introducing state with introduction of a gas. A broken line curve indicates a gradient of a correlation between the detection signal at the signal point A and the detection signal at the background point B. FIG. 7 is a graph of a specific component time series detection signal in the case of introducing ethylene into the sample introducing portion 24. FIG. 8 is an explanatory diagram illustrating a Fourie spectrum of vibration of the specific component time series detection signal. As shown in FIG. 7, the specific component time series detection signal has a smaller noise and more clearly shows introduction of ethylene at the time of about 1.2 seconds, compared with the time series detection signal at the signal point A (shown in FIG. 4). As shown in FIG. 8, Fourier transform of a vibration component of the specific component time series detection signal gives a sharp peak at the frequency of around 33 Hz. This proves that processing the corrected time series detection signal (A-αB) by the low-pass filter, which passes signals with the frequencies of 10 Hz to 30 Hz, is effective.

Figure 9:
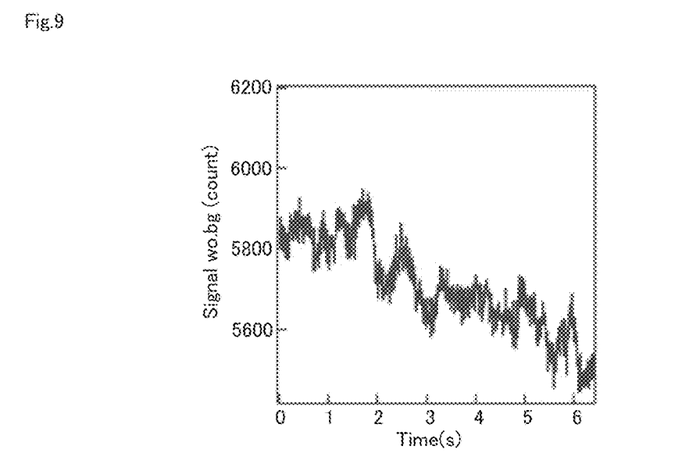
FIG. 9 is a graph of a time series detection signal at the signal point A with regard to methane in the case of introducing a mixed gas of methane and ethylene into the sample introducing portion 24.
Figure 10:
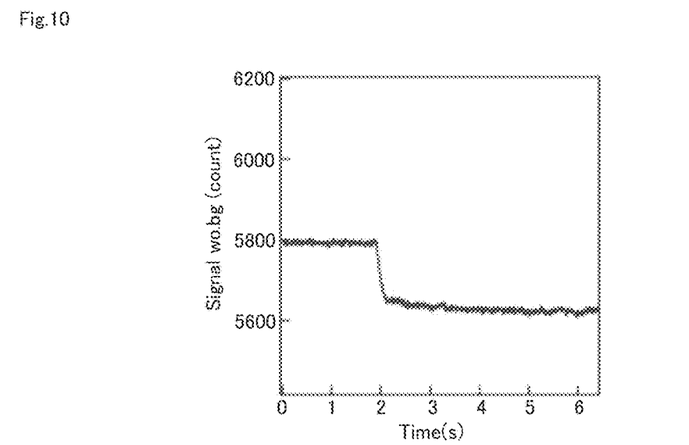
FIG. 10 is a graph of a corrected time series detection signal (A-αB) with regard to methane in the case of introducing the mixed gas of methane and ethylene into the sample introducing portion 24.
Figure 11:
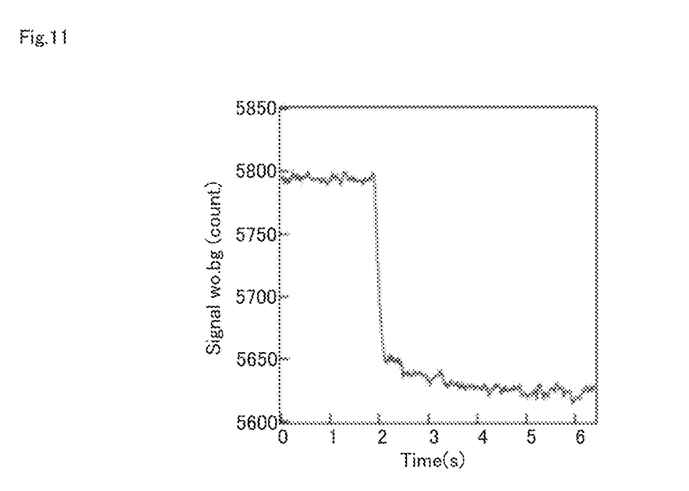
FIG. 11 is a graph of a specific component time series detection signal with regard to methane in the case of introducing the mixed gas of methane and ethylene into the sample introducing portion 24.
Figure 12:
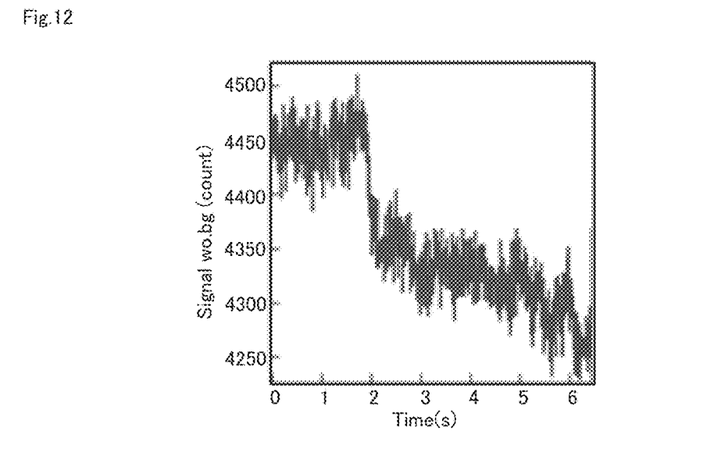
FIG. 12 is a graph of a time series detection signal at the signal point A with regard to ethylene in the case of introducing a mixed gas of methane and ethylene into the sample introducing portion 24.
Figure 13:
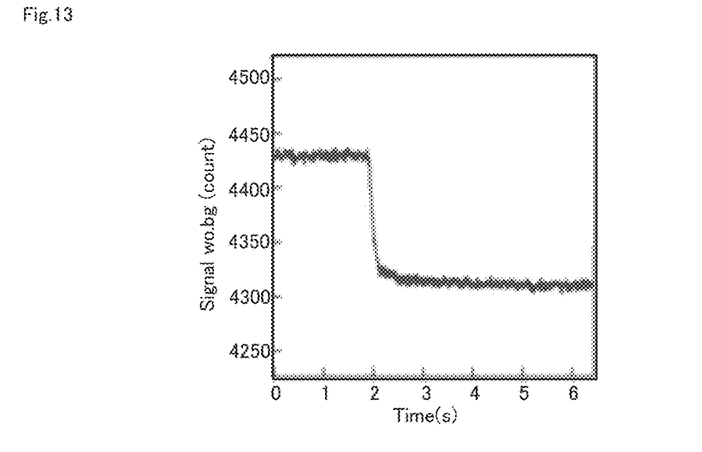
FIG. 13 is a graph of a corrected time series detection signal (A-αB) with regard to ethylene in the case of introducing the mixed gas of methane and ethylene into the sample introducing portion 24.
Figure 14:
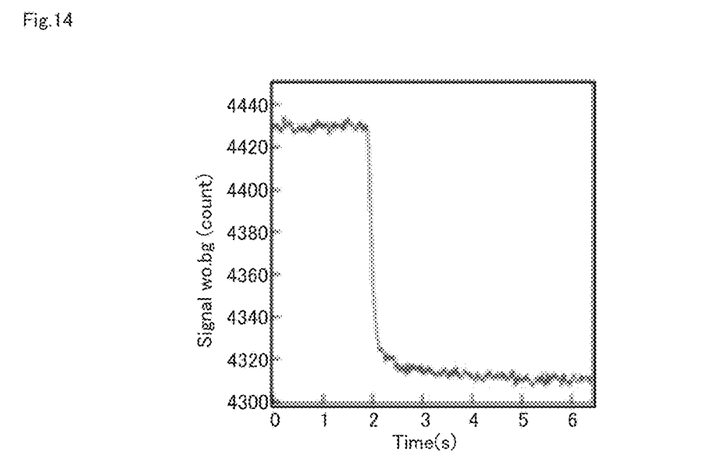
FIG. 14 is a graph of a specific component time series detection signal with regard to ethylene in the case of introducing the mixed gas of methane and ethylene into the sample introducing portion 24.

FIG. 9 is a graph of a time series detection signal at the signal point A with regard to methane in the case of introducing a mixed gas of methane and ethylene into the sample introducing portion 24. FIG. 10 is a graph of a corrected time series detection signal (A-☐B) with regard to methane in the case of introducing the mixed gas of methane and ethylene into the sample introducing portion 24. FIG. 11 is a graph of a specific component time series detection signal with regard to methane in the case of introducing the mixed gas of methane and ethylene into the sample introducing portion 24. FIG. 12 is a graph of a time series detection signal at the signal point A with regard to ethylene in the case of introducing a mixed gas of methane and ethylene into the sample introducing portion 24. FIG. 13 is a graph of a corrected time series detection signal (A-☐B) with regard to ethylene in the case of introducing the mixed gas of methane and ethylene into the sample introducing portion 24. FIG. 14 is a graph of a specific component time series detection signal with regard to ethylene in the case of introducing the mixed gas of methane and ethylene into the sample introducing portion 24. The mixed gas used includes ethane of lower than 12 ppm and ethylene of lower than 12 ppm. As shown in FIG. 9 and FIG. 12, the timing of introduction of the mixed gas is not clearly shown in the time series detection signals at the signal points A of methane and of ethylene in the case of introducing the mixed gas into the sample introducing portion 24. As shown in FIG. 10 and FIG. 13, however, it is clearly shown that the mixed gas is introduced at the timing of 2 seconds in the corrected time series detection signals (A-αB) of methane and of ethylene obtained by subtracting the product of the time series detection signal at the background point B and the correlation coefficient α from the time series detection signal at the signal point A. As shown in FIG. 11 and FIG. 14, it is furthermore clearly shown that the mixed gas is introduced at the timing of 2 seconds in the specific component time series detection signals of methane obtained by processing the corrected time series detection signals (A-αB) by the low-pass filter. As clearly understood from comparison between FIGS. 10 and 13 and FIGS. 11 and 14, the specific component time series detection signals of methane and of ethylene have larger SN ratios and become more prominent at the timing of 2 seconds. In the embodiment with introduction of this mixed gas, as shown in FIG. 13, a fluctuation in the corrected time series detection signal that is a signal after single frame noise rejection is given as 10 counts in peak-to-peak and about 3 counts in root mean square, and a change in signal intensity corresponding to addition of ethylene is about 120 counts. By taking into account the foregoing, the technique of this embodiment allows for detection of a gas having even the concentration of 1 ppm or sub-ppm. This technique also enables a drift of a signal to be removed, thus allowing for long-time accumulation of multiple frames and further enhancing the sensitivity.

As described above, the specific component detection apparatus 20 of the first embodiment specifies the signal point A of the specific component and the background point B, based on the time series two-dimensional spectroscopic image data. The specific component detection apparatus 20 subsequently obtains the corrected time series detection signal (A-αB) by subtracting the product of the time series detection signal at the background point B and the correlation coefficient α between the time series detection signal at the signal point A and the time series detection signal at the background point B from the time series detection signal at the signal point A. This configuration more properly eliminates the influence of background and enables the specific component to be more properly detected. Furthermore, the specific component time series detection signal is obtained by processing the corrected time series detection signal (A-αB) by the low-pass filter. This enables the specific component to be detected furthermore properly. As a result, this enables the specific component included in the gas to be detected with higher sensitivity.

The specific component detection apparatus 20 of the first embodiment employs the specific component detection method including the step of receiving the input of time series two-dimensional spectroscopic image data, the step of specifying the signal point A of the specific component and the background point B based on the time series two-dimensional spectroscopic image data, the step of calculating the correlation coefficient α between the time series detection signal at the signal point A and the time series detection signal at the background point B, and the step of generating the specific component time series detection signal based on the corrected time series detection signal (A-αB), which is obtained by subtracting the product of the time series detection signal at the background point B and the calculated correlation coefficient α from the time series detection signal at the signal point A. Accordingly, this specific component detection method has advantageous effects similar to those of the specific component detection apparatus 20 of the first embodiment, i.e., the advantageous effects of more properly eliminating the influence of background, enabling the specific component to be more properly detected, and enabling the specific component included in the gas to be detected with higher sensitivity.

The specific component detection apparatus 20 of the first embodiment processes the corrected time series detection signal (A-αB) by the low-pass filter to obtain the specific component time series detection signal. A modification may not process the corrected time series detection signal (A-αB) by the low-pass but may use the corrected time series detection signal (A-αB) as the specific component time series detection signal.

The specific component detection apparatus 20 of the first embodiment specifies the signal point A of the specific component and the background point B, based on the time series two-dimensional spectroscopic image data. In the case of using a sample including a plurality of different gases or including a gas of an unknown absorption wavelength, the specific component detection apparatus may be configured to specify a plurality of points having absorption wavelengths among respective points (pixels, areas) constituting a two-dimensional spectroscopic image, as a plurality of signal points A1, A2, . . . , and to specify appropriate points corresponding to the respective signal points A1, A2, . . . over a time period when time series two-dimensional spectroscopic image data is obtained, among the respective points constituting the two-dimensional spectroscopic image, as background points B1, B2, . . . . One available procedure may select a point having a wavelength of minimum absorption over the time period when time series two-dimensional spectroscopic image data is obtained, as the background point B. Another available procedure may select a point having a maximum correlation coefficient relative to a target signal point (one of the signal points A1, A2, . . . ), as the background point B. Additionally, a plurality of background points may be selected relative to one signal point. This enables each specific component to be detected with high sensitivity.

The following describes a determination apparatus 120 according to a second embodiment. The determination apparatus 120 of the second embodiment has a similar hardware configuration to that of the specific component detection apparatus 20 of the first embodiment, except a different process performed by the arithmetic unit 30. In order to avoid duplicated explanation, the following describes a process performed by the arithmetic unit 30 with omission of the description of the hardware configuration of the determination apparatus 120 of the second embodiment.

Figure 15:
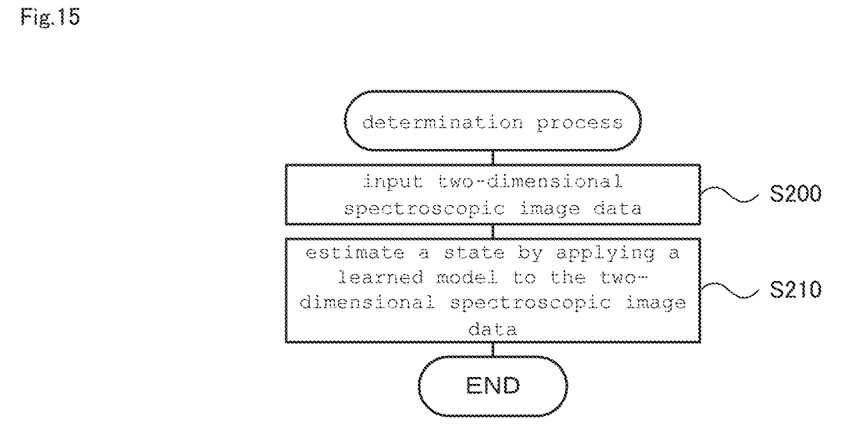
FIG. 15 is a flowchart showing one example of a determination process performed by the arithmetic unit 30 in a determination apparatus 120 according to a second embodiment.

The arithmetic unit 30 in the determination apparatus 120 of the second embodiment performs a determination process illustrated in FIG. 15. The determination process first receives an input of two-dimensional spectroscopic image data detected by the detector 28 (step S200). The two-dimensional spectroscopic image data means one two-dimensional spectroscopic image data within time series, out of the time series two-dimensional spectroscopic image data used in the first embodiment. The determination process subsequently applies a learned model to the two-dimensional spectroscopic image data, so as to estimate a state (step S210) and is then terminated.

Figure 16:
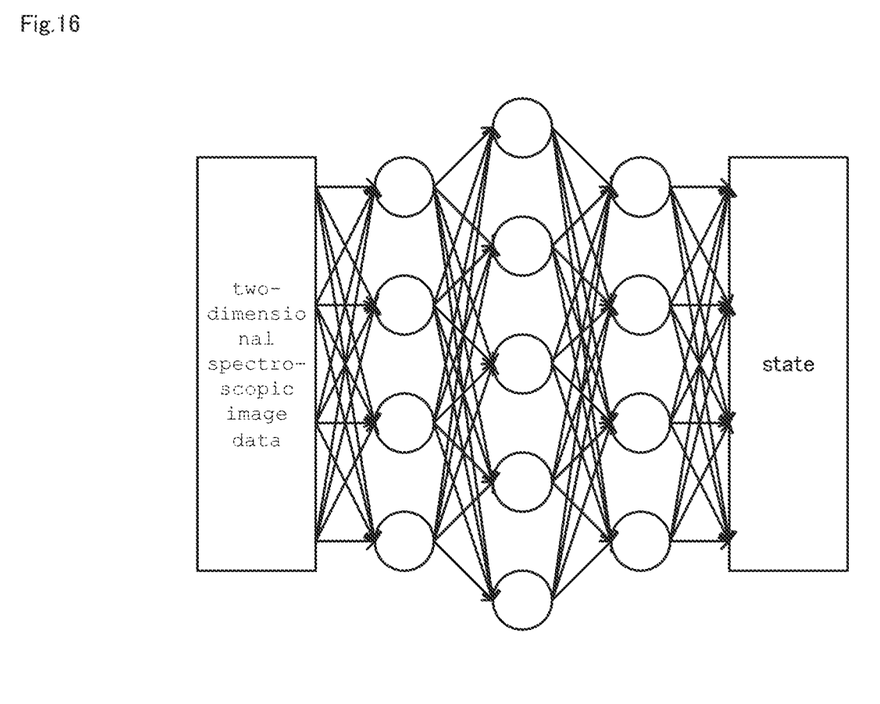
FIG. 16 is an explanatory diagram illustrating one example of a deep learning model using a plurality of two-dimensional spectroscopic image data as an input data set and a state at that time as teacher data.

The learned model is obtained by machine learning, such as deep learning, that uses a plurality of two-dimensional spectroscopic image data as an input data set and a state at that time as teacher data. FIG. 16 illustrates one example of a deep learning model using a plurality of two-dimensional spectroscopic image data as an input data set and a state at that time as teacher data.

The determination apparatus 120 of the second embodiment may serve as an apparatus for diagnosing a disease name based on expiration by using "expiration" as the "gas" of an inspection object and using the "name of disease" as the "state", may serve as an apparatus for checking the state of an engine based on a combustion gas by using the "combustion gas of the engine" as the "gas" of an inspection object and using the "state of the engine" as the "state", and may serve as an apparatus for checking the comfort of a closed space such as a private room based on the air in the space by using the "air in the closed space such as the private room" as the "gas" of an inspection object and using the "comfort of a person who is present in the closed space such as the private room" as the "state". In an example of application, the apparatus may be installed in a vehicle and may be used for the purpose of health care check during driving. In another example of application, the apparatus may be installed in a conference hall or a shop and may be used for the purpose of security, such as detection of explosives.

As described above, the determination apparatus 120 of the second embodiment applies a learned model, which is obtained by machine learning using a plurality of two-dimensional spectroscopic image data as an input data set and a state as teacher data, to the two-dimensional spectroscopic image data, so as to estimate a state. This configuration enables the state to be determined more properly.

The determination apparatus 120 of the second embodiment employs the determination method of applying a learned model, which is obtained by machine learning using a plurality of two-dimensional spectroscopic image data as an input data set and a state as teacher data, to the two-dimensional spectroscopic image data, so as to estimate the state. Accordingly, this determination method has advantageous effects similar to those of the determination apparatus 120 of the second embodiment, i.e., the advantageous effect of enabling the state to be determined more properly.

The determination apparatus 120 of the second embodiment determines the state by using the learned model that is obtained by machine learning using a plurality of two-dimensional spectroscopic image data as an input data set and a state as teacher data. The determination apparatus may, however, be configured to perform machine learning by using a plurality of two-dimensional spectroscopic image data as an input data set and a state as teacher data.

The aspect of the disclosure is described above with reference to the embodiment. The disclosure is, however, not limited to the above embodiment but various modifications and variations may be made to the embodiment without departing from the scope of the disclosure.

INDUSTRIAL APPLICABILITY

The technique of the disclosure is preferably applicable to the manufacturing industries of the specific component detection and determination apparatuses and so on.

The invention claimed is:

1. A specific component detection method of properly detecting a time series detection signal of a specific component included in a gas, the specific component detection method comprising:
   an input step of receiving an input of time series two-dimensional spectroscopic image data of the gas;
   a specification step of specifying a signal point of the specific component and a background point, based on the time series two-dimensional image data;
   a correlation coefficient calculation step of calculating a correlation coefficient between a time series detection signal at the signal point and a time series detection signal at the background point; and
   a signal generation step of generating a time series detection signal of the specific component, based on a corrected time series detection signal obtained by subtracting a product of the correlation coefficient and the time series detection signal at the background point from the time series detection signal at the signal point.

2. The specific component detection method according to claim 1,
   wherein the signal generation step comprises a step of processing the corrected time series detection signal by a low-pass filter, so as to generate the time series detection signal of the specific component.

3. The specific component detection method according to claim 1,
   wherein the time series two-dimensional spectroscopic image data comprises data obtained by a high order diffraction grating configured to disperse light to high order diffraction light and a spectrometer placed at a location where high order diffraction lights obtained by the high order diffraction grating overlap with each other.

4. The specific component detection method according to claim 3,
   wherein the high order diffraction grating is an Echelle diffraction grating.

5. A specific component detection apparatus configured to detect a specific component by using the specific component detection method according to claim 1.

6. The specific component detection apparatus according to claim 5, comprising:
   a light source configured to irradiate a gas including a detection object with mid-infrared light;
   a two-dimensional spectroscopic diffractometer configured to two-dimensionally disperse and diffract mid-infrared light radiated from the light source and transmitted through the gas; and
   an arithmetic unit configured to generate a time series detection signal of the specific component, based on time series two-dimensional spectroscopic image data obtained by the two-dimensional spectroscopic diffractometer.

7. A determination method of determining a state based on a component included in a gas, the determination method comprising:
   applying a learned model, which is obtained by machine learning using a plurality of two-dimensional spectroscopic image data of the gas as an input data set and a state based on the component in the gas as teacher data, to two-dimensional spectroscopic image data of the gas, so as to estimate a state.

8. The determination method according to claim 7,
   wherein the two-dimensional spectroscopic image data comprises data obtained by a high order diffraction grating configured to disperse light to high order diffraction light and a spectrometer placed at a location where high order diffraction lights obtained by the high order diffraction grating overlap with each other.

9. The determination method according to claim 8,
   wherein the high order diffraction grating is an Echelle diffraction grating.

10. The determination method according to claim 7,
wherein the plurality of two-dimensional spectroscopic image data of the gas comprise a plurality of time series two-dimensional spectroscopic image data of the gas.

11. A determination apparatus configured to determine a state by using the determination method according to claim 7.

12. The determination apparatus according to claim 11, comprising:
   a light source configured to irradiate a gas including a detection object with mid-infrared light;
   a two-dimensional spectroscopic diffractometer configured to two-dimensionally disperse and diffract mid-infrared light radiated from the light source and transmitted through the gas; and
   an arithmetic unit configured to estimate a state, based on two-dimensional spectroscopic image data obtained by the two-dimensional spectroscopic diffractometer.

* * * * *